United States Patent [19]
Koehler et al.

[11] Patent Number: 5,786,502
[45] Date of Patent: Jul. 28, 1998

[54] PROCESS FOR PREPARING DIESTERS OF HIGHER α,ω-DICARBOXYLIC ACIDS

[75] Inventors: Guenther Koehler; Josef Metz, both of Marl, Germany

[73] Assignee: Huels Aktiengesellschaft, Marl, Germany

[21] Appl. No.: 871,586

[22] Filed: Jun. 9, 1997

[30] Foreign Application Priority Data

Jun. 13, 1996 [GB] United Kingdom ............... 19623585

[51] Int. Cl.⁶ ........................... C07C 69/34; C07C 67/00
[52] U.S. Cl. ........................................ 560/190; 560/204
[58] Field of Search ............................... 560/190, 204

[56] References Cited

U.S. PATENT DOCUMENTS

| | | | |
|---|---|---|---|
| 2,811,551 | 10/1957 | Coffman et al. | 260/537 |
| 3,290,367 | 12/1966 | White et al. | 260/531 |
| 3,574,756 | 4/1971 | Sheehan et al. | 260/586 |
| 4,689,344 | 8/1987 | Bar-Tana | 514/527 |
| 5,436,365 | 7/1995 | Kohler | 560/204 |
| 5,453,535 | 9/1995 | Fischer | 560/190 |

FOREIGN PATENT DOCUMENTS

| | | |
|---|---|---|
| 0 643 036 A1 | 6/1994 | European Pat. Off. . |
| 0 632 010 A1 | 8/1994 | European Pat. Off. . |
| 1 668 730 | 1/1971 | Germany . |

*Primary Examiner*—Samuel Barts
*Assistant Examiner*—Rosalynd Keys
*Attorney, Agent, or Firm*—Oblon, Spivak, McClelland, Maier & Neustadt, P.C.

[57] ABSTRACT

A process is provided for preparing diesters of higher α,ω-dicarboxylic acids from cycloaliphatic ketones and carbonic diesters in the presence of a strongly basic agent, which involves continuously feeding a cycloaliphatic ketone having 8 to 20 ring members, at least an equimolar amount of a carbonic diester and a catalytic amount of a strongly basic agent to a reaction zone in which condensation occurs between the cycloaliphatic ketone and the carbonic diester to give the corresponding cyclic β-keto acid ester enolate, which is then ring-opened by the released alcohol to give the α,ω-dicarboxylic diester and from which reaction mixture is continuously taken off.

15 Claims, No Drawings

5,786,502

PROCESS FOR PREPARING DIESTERS OF HIGHER α,ω-DICARBOXYLIC ACIDS

BACKGROUND OF THE INVENTION

1. Field of the Invention

The present invention relates to an improved process for preparing diesters (or neutral esters) of α,ω-dicarboxylic acids from cyclic ketones and carbonic esters in the presence of a strongly basic agent.

2. Discussion of the Background

Diesters of higher α,ω-dicarboxylic acids, such as dialkyl brassylates, are valuable intermediates for preparing a variety of useful compounds, such as aroma compounds, active compounds for medicaments, crop protection agents and oligoesters or polyesters. For example, the cyclic ester of brassylic acid (which has 13 carbon atoms) with ethylene glycol is a synthetic musk-like aroma compound which is used in perfumery and cosmetics.

The laid-open German Patent Application 16 68 730 describes the preparation of dialkyl brassylates by reacting cyclododecanone with a dialkyl carbonate, using a strongly basic agent, which is preferably used in a ratio of about 1 mol per mole of cyclododecanone. Suitable strongly basic condensation agents mentioned are potassium, lithium and their alcoholates. In the examples, sodium, sodium methylate, sodium ethylate and lithium are used. The reaction mixture is worked up by acidification with mineral acid, so that stoichiometric amounts of salts are formed as by-product. The process operates batchwise and gives yields of dialkyl brassylates of 85 to 88% of theory. The overall reaction—stages (1) and (2)—of the synthesis of dimethyl brassylate (II) by reacting cyclododecanone with dimethyl carbonate using sodium methylate as the strongly basic agent and acidification of the reaction mixture with hydrochloric acid may be described by the following scheme:

(1)

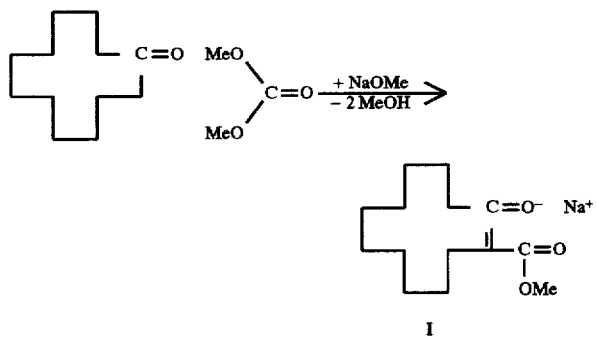

(2)

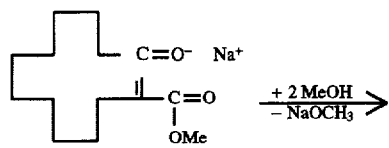

-continued

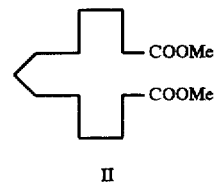

(3)

NaOCH₃ + HCl ⟶ NaCl + CH₃OH

Reaction (1), the condensation of cyclododecanone to give the β-keto acid ester (I), shown in the form of its sodium enolate in the scheme above, has already been described by S. J. Rhoads et al. in *Tetrahedron*, 19, 1625 (1963). The basic condensation agent used in this case was sodium hydride.

However, a disadvantage in the process according to the laid-open German Patent Application is that due to the use of sodium or sodium-containing basic condensation agents in molar amounts, the rheological properties of the reaction mixture are unfavorable. Thixotropic suspensions are formed which range from difficult to stir to almost rigid. Such suspensions can only be dealt with using considerable resources, especially on an industrial scale.

Substantial amounts of by-products are also formed in this reaction scheme, such as dialkyl ethers, which escape in the vapor state, and the sodium salt of the monoalkyl carbonate, which remains in the solid state. Both types of by-products lead to disposal problems in an industrial scale preparation, as do the sodium salts which are produced in molar amounts in the neutralization of the reaction mixture with mineral acid.

SUMMARY OF THE INVENTION

Accordingly, one object of the present invention is to provide a method for the preparation of diesters of higher α,ω-dicarboxylic acids that can be readily performed on an industrial scale without rheological problems occurring in the reaction mixture.

A further object of the present invention is to provide a method for the preparation of such diesters that gives significantly improved yields compared to conventional processes.

These and other objects of the present invention have been satisfied by the discovery of a method for the preparation of diesters of higher α,ω-dicarboxylic acids comprising continuously feeding a cycloaliphatic $C_8$–$C_{20}$ ketone, at least an equimolar amount of a carbonic diester and a catalytic amount of a strongly basic agent to a reaction zone in which condensation of the cycloaliphatic ketone with the carbonic diester takes place to give the corresponding cyclic β-keto acid ester enolate, which is ring-opened by the released alcohol to give the α,ω-dicarboxylic diester and from which the reaction mixture is continuously taken off.

DETAILED DESCRIPTION OF THE PREFERRED EMBODIMENTS

The present invention relates to a method for the preparation of diesters of higher α,ω-dicarboxylic acids comprising continuously feeding a cycloaliphatic $C_8$–$C_{20}$ ketone, at least an equimolar amount of a carbonic diester and a catalytic amount of a strongly basic agent (preferably having a pH>10) to a reaction zone in which condensation of the cycloaliphatic ketone with the carbonic diester takes place to give the corresponding cyclic β-keto acid ester enolate, which is ring-opened by the released alcohol to give the α,ω-dicarboxylic diester and from which the reaction mixture is continuously taken off.

The process according to the present invention is preferably performed by subdividing the reaction zone into at least two partial-reaction zones, removing low-boiling portions from the reaction mixture in at least one partial-reaction zone and feeding alcohol to the reaction mixture in at least one later partial-reaction zone. Within the context of the present invention, the term "later partial-reaction zone" refers to a partial reaction zone that is more downstream in the reaction process than the partial-reaction zone from which low-boiling portions are removed from the reaction mixture.

The preferred strongly basic agents for use in the present process are potassium and strongly basic potassium compounds.

The process according to the present invention gives higher yields, typically more than 90% of theory, than the process according to the prior art. Since only catalytic amounts of strongly basic agent are required, the rheological problems encountered in the conventional process are less pronounced and can be dealt with without special measures, even on an industrial scale. This especially applies if the strongly basic agent used is potassium or strongly basic potassium compounds. Surprisingly, the rheological properties of the reaction mixtures are then considerably improved again in comparison with a procedure using the equivalent amounts of sodium or sodium compounds under otherwise identical conditions. The ability to reduce the amounts of strongly basic agent used in the present process to only catalytic amounts also represents a cost advantage in comparison with the conventional procedure using molar amounts and, furthermore, leads to a reduced formation of byproducts, such as dialkyl ethers and salts of the carbonic monoester, and of salts in the neutralization of the strongly basic agent.

The energy balance of the process according to the present invention is also markedly more favorable than that of the known batchwise procedure. When the cycloaliphatic ketone is mixed with the carbonic diester and the strongly basic agent, a considerable amount of heat is liberated. For example, in the case of molar amounts of cyclododecanone, dimethyl carbonate and sodium methylate, this is −30 kJ per mole of cyclododecanone. In the conventional batchwise process, the mixture must be cooled initially and heated at the end of the reaction. The changeover which this requires from cooling to heating is demanding in terms of control and safety systems and furthermore wastes a lot of energy. The continuous process according to the present invention, in contrast, operates virtually adiabatically and isothermally. In the steady state, only a small constant amount of heat needs to be supplied.

The present process starts with cycloaliphatic ketones having 8 to 20 carbon atoms and at least one α-methylene group and leads to diesters of α,ω-dicarboxylic acids which have one carbon atom more than the starting ketone, i.e. from 9 to 21 carbon atoms. Preferred starting ketones are cycloalkanones having 8 to 20 carbon atoms, more preferably 10 to 16 carbon atoms. Suitable examples include cyclooctanone, cyclodecanone, cyclododecanone, cyclopentadecanone, cyclohexadecanone, cyclooctadecanone and cycloeicosanone.

Carbonic diesters which are suitable for the process according to the present invention include the esters having two, identical or different, hydrocarbon radicals bound via oxygen to the carbonyl carbon. Suitable examples of the hydrocarbon radicals include alkyl, cycloalkyl, aralkyl, alkaryl or aryl radicals, each having from 1 to 10 carbons per radical. Particular preference is given to dialkyl carbonates having identical alkyl radicals each having 1 to 6 carbon atoms. The carbonic diesters supply one of the two carboxylic ester groups of the α,ω-dicarboxylic diester to be prepared. Suitable carbonic diesters for use in the present invention include dimethyl carbonate, diethyl carbonate, diisopropyl carbonate, di-n-butyl carbonate, dicyclopentyl carbonate, dibenzyl carbonate, diphenyl carbonate and di-p-tolyl carbonate. The carbonic diester should be used in at least equimolar amounts, based on the cycloaliphatic ketone. If desired, an excess can be used, for example up to 2.5 times the molar amount, and that excess acts as a solvent and diluent.

Of the strongly basic agents which can catalyze the reaction, potassium and strongly basic potassium compounds are particularly preferred. Suitable strongly basic potassium compounds include alcoholates of $C_1$–$C_{10}$ hydrocarbon alcohols, such as potassium methylate, potassium ethylate, potassium isopropylate, potassium n-butylate and potassium benzylate, and also potassium amide and potassium hydride. Other suitable strongly basic substances are sodium and lithium and the sodium and lithium compounds corresponding to the above potassium compounds. If an alkali metal alcoholate is used, it is preferred that it be derived from the alcohol whose carbonic diester supplies one of the two carboxylic ester groups of the α,ω-dicarboxylic diester to be prepared. Otherwise, the formation of mixed esters of the α,ω-dicarboxylic acid in question must be expected. While such mixed esters are included within the present invention, they are not preferred.

An essential feature of the present process is that the strongly basic agent must be used in catalytic amounts only. Preferably, it is used in an amount of 0.05 to 0.5, more preferably 0.1 to 0.3, equivalents per mole of cycloaliphatic ketone.

The process according to the present invention can be carried out in the presence of inert solvents and diluents. Within the context of the present invention, the term "inert", as it relates to solvents or diluents, indicates that the solvent or diluent either undergoes no reaction with other components of the reaction mixture or undergoes no observable reaction with components of the mixture (for example, use of dimethyl carbonate as solvent and as the dialkyl carbonate would be considered "inert" as a solvent, since it would not undergo observable reaction with methanol released during reaction or with an alkali metal methylate catalyst). This is particularly advisable if only a small excess of carbonic diester is used. Inert solvents and diluents also facilitate the feed of alcoholates or other pulverulent strongly basic agents, since suspensions can be added more readily, and with greater control of the amount added, than powders. Suitable inert solvents and diluents include glycol ethers, such as ethylene glycol diethyl ether and triethylene glycol dimethyl ether, N-substituted carboxylic amides, such as dimethylformamide and N-methylpyrrolidone, or the dialkyl carbonate used as the reaction partner which does not enter into a reaction with the alcoholates. Generally, inert solvents and diluents, if they are used, are used in amounts of about 5 to about 50 percent by weight, preferably about 15 to about 40 percent by weight, based on the total reaction mixture.

If the present process invention is carried out in only one reaction zone, the reactions corresponding to the above part-reactions (1) and (2) proceed together. The cycloaliphatic ketone, the carbonic diester, and the strongly basic agent (if desired as a suspension in an inert solvent and diluent) are introduced continuously into the reaction zone in the amounts specified and the equivalent amount of reaction mixture is continuously taken off. The temperatures in the reaction zone depend on the particular starting materials and the desired residence time. They are preferably 40° to 160° C., more preferably 60° to 120° C., and are maintained in the steady state, as mentioned, by supply of a small amount of heat. The mean residence times are, depending on starting materials and reaction temperature, generally 2 to 10 hours, preferably 3 to 8 hours.

Particularly favorable results are achieved if the reaction zone is subdivided into at least two partial-reaction zones, wherein low-boiling portions are removed from the reaction mixture in at least one early or first partial-reaction zone and alcohol is fed to the reaction mixture in at least one later or last (that is downstream in the reaction sequence) partial-reaction zone. In this manner, the above overall reaction (1) and (2) is subdivided in such a manner that the partial-reaction (1) essentially proceeds in the first partial-reaction zone (in which low-boilers are taken off) and the reaction (2) essentially proceeds in a second, later partial-reaction zone (into which alcohol is fed). If the reaction zone is therefore subdivided into three partial-reaction zones and no low-boiling portions are taken off in the first partial-reaction zone, this must take place in the second partial-reaction zone and alcohol must be fed to the reaction mixture in the third partial-reaction zone.

The low-boiling portions are predominantly carbonic diesters, alcohol released in partial-reaction (1) as well as ethers and other by-products which are also formed to a lesser extent in the present process. These low-boiling portions can be worked up continuously or batchwise by distillation, whereupon the carbonic diester can be recycled to the first partial-reaction zone and the alcohol can be recycled to a second and/or any further partial-reaction zones. Obviously, it is also possible to feed fresh alcohol to the reaction mixture in the second and/or any further partial-reaction zones. In any case, it is preferred to feed the alcohol corresponding to the carbonic diester used, to avoid the production of generally unwanted mixed diesters of the α,ω-dicarboxylic acid in question. However, as noted above, the mixed diesters are included within the scope of the present invention since they are just as, or similarly, useful as the diesters having identical alcohol radicals for some purposes. However, generally, the latter are preferred.

With respect to the reaction temperatures, the procedure with partial-reaction zones does not differ significantly from the procedure with only one reaction zone. They are therefore generally 40° to 160° C., preferably 60° to 120° C. It is preferred here to set the temperature in the partial-reaction zone or zones in which alcohol is fed somewhat higher than in the partial-reaction zone or zones in which low-boiling portions are removed from the reaction mixture. As in the embodiment of the present process with only one reaction zone, in the case of the variant with a subdivided reaction zone, a small amount of energy must also be fed in the steady state. More precisely, more energy must be fed to the later partial-reaction zone or zones than to the earlier partial-reaction zone or zones. The optimum temperatures in the individual partial-reaction zones depend, inter alia, on the particular reaction partners and may be determined without difficulty by preliminary experiments.

Generally, atmospheric pressure prevails in the partial-reaction zones (as is also the case with the embodiment of the present process with only one reaction zone). If, in the interest of a high reaction rate, temperatures at the upper end of the ranges are selected and esters of low-boiling alcohols are to be prepared, elevated pressures, such as from 2 to 10 bar, may also be employed. The mean residence times in the individual partial-reaction zones can vary in broad ranges and are generally between 30 minutes and 20 hours, preferably from 1 hour to 10 hours. It is preferable to provide shorter residence times for the first or the early partial-reaction zones than for the last or the later partial-reaction zones.

The process according to the present invention with only one reaction zone can be carried out in any conventional reactor, such as in a stirred tank to which the starting materials including the strongly basic agent and, if appropriate, an inert solvent and diluent are continuously fed in the desired weight ratio. The reaction zone is then the interior of the stirred tank. Generally, the reaction parameters, such as amounts of starting materials, reaction temperature and mean residence time, can be matched to one another in such a manner that the reaction, in the steady state, proceeds isothermally and, at the same time, virtually adiabatically. However, a reactor having means for heating and cooling is preferable, because it offers the desired flexibility in the reaction procedure, and provides an added safety measure.

The present process with two or more partial-reaction zones can be carried out in any conventional multi-zone reactors, such as in a cascade of two or more sequential stirred reactors. In this case, the cycloaliphatic ketone, the carbonic diester, the strongly basic agent and, if desired, an inert solvent and diluent are continuously fed to the first reactor in the weight ratios specified. From the first, or one of the following, reactors of the cascade, low-boiling portions are distilled off and condensed. The amount of the low-boilers distilling off inevitably follows from the type and amount of the starting materials and the temperature and pressure which prevail in the first part-reaction zone. It is generally 50 to 250 g per liter of reaction mixture per hour. The low-boilers are worked up by distillation batchwise or continuously. The carbonic diester is recycled to the first reactor, expediently together with the starting materials. The alcohol is fed to the next, or a subsequent, reactor.

As soon as the desired filling level is achieved in the first reactor, an amount of reaction mixture is taken off which corresponds to the amount of starting materials supplied (if appropriate minus the low-boilers which have distilled off) and transferred to a second reactor. The low-boilers can then be distilled off from this mixture, if this has not already occurred in the first reactor. Otherwise, alcohol is fed to this reactor, and, if appropriate, to further reactors of the cascade. Preferably, the amount of alcohol added is from 10 to 50 parts by weight per part by weight of cycloaliphatic ketone used. If alcohol is fed to a plurality of reactors of the cascade, its total amount can be subdivided in the ratio of the volumes of the reactors and thus the mean residence times.

The reaction mixture which leaves the single reactor (in the embodiment of the process with only one reaction zone), or the last reactor of the cascade in embodiments having a plurality of partial-reaction zones, is generally sufficiently mobile at temperatures around 50° C. to be readily conveyed by mechanical pumping. If desired, inert solvents or diluents such as toluene, xylene or diethylene glycol dimethyl ether may be added, in order to keep the mixture pumpable. This is particularly advisable if the α,ω-dicarboxylic diester prepared, which is produced in a concentrated solution, has a relatively high melting point. Dimethyl brassylate, for example, melts at 33°–35° C.

Readily volatile portions can be separated off from the reaction mixture continuously or batchwise, such as by means of a conventional thin-film evaporator. These volatile portions predominantly comprise alcohol and carbonic diester and are recycled to the process. The residue from the thin-film evaporator can be separated in a second separation step, such as a short-path distillation, into the desired α,107-dicarboxylic diester and a residue which is still higher boiling or no longer distillable. The residue contains the strongly basic agent and can be recycled to the single reactor or the first reactor of the cascade. Preferably, however, a part of the residue is eliminated in order to remove undesired and, possibly, interfering high-boiling or non-distillable by-products from reintroduction into the process.

Alternatively, the reaction mixture which leaves the single reactor or the last reactor of the cascade can be treated with water, in which case two phases form which can be easily separated from one another. The lower aqueous phase contains relatively small amounts of salt, because the strongly basic agent was only used in catalytic amounts. It can therefore be disposed of or worked up in an environmentally acceptable manner without great resources. The upper organic phase can be purified by distillation without complex separation equipment.

EXAMPLES

Having generally described this invention, a further understanding can be obtained by reference to certain specific examples which are provided herein for purposes of illustration only and are not intended to be limiting unless otherwise specified.

Example 1

182 g (1 mol) of cyclododecanone, 162 g (1.8 mol) of dimethyl carbonate and a suspension of 14 g (0.2 mol) of potassium methylate powder in 100 g of triethylene glycol dimethyl ether were metered per hour into a 1 liter double-walled glass reactor (first reactor) equipped with temperature control, agitator and distillation attachment. The substances were mixed by stirring and the temperature was initially kept at 90° C. by cooling. After one hour, the intended filling level in the reactor was achieved and the distillation of the low-boilers and the take-off of reaction mixture was begun. The mean residence time in the first reactor was therefore 1 hour. Approximately 50 g of low-boilers were taken off per hour, which comprised approximately 25% of dimethyl carbonate and approximately 75% methanol. The low-boilers could be worked up to recover these constituents. After about 4 hours, a steady state prevailed in the first reactor, and a small supply of heat was necessary to maintain the temperature of 80° C.

Enough reaction product was taken off from the first reactor to maintain the filling level and was conveyed by means of a metering pump into a second 5 liter capacity glass reactor (second reactor). After 8 hours, the intended filling level in the second reactor was achieved and the take-off of approximately 460 g/h of reaction product was begun for the work-up, so that the filling level was maintained. The mean residence time in the second reactor was therefore about 8 hours. The reaction mixture was kept at 90°–100° C., and 50 g of methanol were introduced per hour into the second reactor.

After approximately 2 hours, calculated from the beginning of the feed of reaction mixture from the first reactor, a steady state also prevailed in the second reactor. The approximately 460 g/h of reaction mixture were fractionated by means of a laboratory thin-film evaporator into a low-boiler mixture, essentially comprising methanol and dimethyl carbonate, and a bottom discharge. This bottom discharge was separated in a second distillation step via a short-path distillation at 1 hPa into a distillable fraction (top temperature rising from 95° to 135° C.) and a non-distillable residue. From the distillable fraction, in a subsequent fractional distillation, in addition to the triethylene glycol dimethyl ether, 252 g of dimethyl brassylate of b.p. 112° C./0.5 hPa, m.p. 34°–35° C. with a purity (according to GC analysis) of 99% were obtained. The yield, based on cyclododecanone used, was 92% of theory.

Example 2

14 g (0.2 mol) of potassium methylate powder were added in the course of one hour to a mixture of 182 g (1 mol) of cyclododecanone and 144 g (1.6 mol) of dimethyl carbonate in a 2 liter double-walled glass reactor equipped with a powder charging device (first reactor). The temperature was maintained at 60° C. during this operation by cooling. After this base mixture was prepared, 56 g (0.8 mol) of potassium methylate, 728 g (4 mol) of cyclododecanone and 576 g (6.4 mol) of dimethyl carbonate were added per hour. After about 2 hours, a steady state was achieved, in which the reactor was kept at a temperature of 60° C. by a low supply of heat. Approximately 1388 g of reaction mixture were taken off per hour from the first reactor, so that the filling level was maintained. The mean residence time was therefore about 1 hour.

The discharge from the first reactor was transferred to a 10 liter reactor equipped with distillation attachment (second reactor). The temperature of the mixture was kept at 100° C., and approximately 200 g of low-boilers, which included methanol and dimethyl carbonate, were taken off per hour by the distillation attachment. After 8 hours, the intended filling level in the second reactor was achieved. The removal of 1200 g/h of reaction mixture was begun, so that the filling level was maintained. The mean residence time in the second reactor was therefore about 8 hours. After about 10 hours, calculated from the beginning of the feed of reaction mixture into the second reactor, a steady state was established.

The reaction mixture taken off from the second reactor was transferred into a 5 liter reactor (third reactor), in which a temperature of 70° C. was maintained by heat supply. 100 g/h of methanol were additionally fed to the third reactor. After about 2 hours, the intended filling level was achieved, and after a further 2 hours a steady state was established. The mean residence time was about 2 hours. 1300 g of reaction mixture, which were worked up as in Example 1, were taken off per hour from the third reactor. Dimethyl brassylate was obtained at a purity (according to GC) of 98.1%. The yield, based on the 4 mol of cyclododecanone fed per hour, was 91% of theory.

Example 3

The procedure of Example 2 was followed, except that 100 g (1.2 mol) of potassium methylate, 728 g (4 mol) of cyclododecanone and 849 g (7.2 mol) of diethyl carbonate were fed to the first reactor per hour. Instead of 100 g/h of methanol, 120 g/h of ethanol were fed to the reactor. 1116 g of diethyl brassylate were obtained per hour, equivalent to a yield of 93% of theory, based on cyclododecanone used.

Example 4

The procedure of Example 1 was followed, except that instead of potassium methylate powder, a suspension of 14 g (0.2 mol) of potassium methylate powder in 80 g (0.9 mol) of dimethyl carbonate was fed by means of a metering pump to the first reactor. At the same time, a mixture of 100 g (1.1 mol) of dimethyl carbonate and 182 g (1 mol) of cyclododecanone was fed to the first reactor. 250 g of dimethyl brassylate were obtained per hour, equivalent to a yield of 92% of theory, based on cyclododecanone used.

This application is based on German Patent Application 196 23 585.5, filed with the German Patent Office on Jun. 13, 1996, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing a diester of higher α,ω-dicarboxylic acids comprising:

continuously feeding a cycloaliphatic ketone having 8 to 20 ring members, at least an equimolar amount of a carbonic diester and a catalytic amount of a strongly basic agent to a reaction zone, wherein said catalytic amount of said strongly basic agent is an amount of from 0.05 to 0.5 equivalents per mole of cycloaliphatic ketone wherein condensation of the cycloaliphatic ketone with the carbonic diester to give a cyclic β-keto acid ester enolate and ring-opening of the cyclic β-keto acid ester enolate by an alcohol to give the α,ω-dicarboxylic diester take place in said reaction zone and continuously removing an amount of the resulting reaction mixture from the reaction zone in an amount sufficient to maintain a steady state level of reaction mixture in the reaction zone.

2. The process as claimed in claim 1, wherein the reaction zone is subdivided into at least two partial-reaction zones, in a reaction sequence wherein low-boiling portions are removed from the reaction mixture in at least one of said partial-reaction zones and alcohol is fed to the reaction mixture in at least one partial-reaction zone later in the reaction sequence than said partial reaction zone from which low-boiling portions are removed.

3. The process as claimed in claim 1, wherein the strongly basic agent is potassium or a strongly basic potassium compound.

4. The process as claimed in claim 1, wherein the strongly basic agent is a potassium alkanolate of an alcohol containing from 1 to 10 carbon atoms.

5. The process as claimed in claim 1, wherein the strongly basic agent is potassium methylate.

6. The process as claimed in claim 1, wherein the cycloaliphatic ketone is cyclododecanone.

7. The process as claimed in claim 1, wherein the carbonic diester is an ester of carbonic acid with an alkanol having 1 to 6 carbon atoms.

8. The process as claimed in claim 1, wherein the carbonic diester is dimethyl carbonate.

9. The process as claimed in claim 1, wherein the condensation is performed in the reaction zone at a temperature of from 40° to 160° C.

10. The process as claimed in claim 1, wherein the condensation is performed in the reaction zone at a temperature of from 60° to 120° C.

11. The process as claimed in claim 1, wherein the strongly basic agent is introduced into the reaction zone as a suspension in an inert solvent and diluent.

12. The process as claimed in claim 1, wherein an inert solvent and diluent is added to the reaction mixture after removal from the reaction zone to improve the pumpability.

13. The process as claimed in claim 2, wherein each partial reaction zone is operated at a temperature of from 40° to 160° C.

14. The process as claimed in claim 1, wherein said strongly basic agent is present in an amount of from 0.1 to 0.3 equivalents per mole of cycloaliphatic ketone.

15. The process as claimed in claim 1, wherein the alcohol is added to the reaction zone at an amount of from 10 to 50 parts by weight per part by weight of cycloaliphatic ketone.

* * * * *

UNITED STATES PATENT AND TRADEMARK OFFICE
CERTIFICATE OF CORRECTION

PATENT NO. : 5,786,502
DATED : July 28, 1998
INVENTOR(S) : Guenther KOEHLER, et al.

It is certified that error appears in the above-identified patent and that said Letters Patent is hereby corrected as shown below:

On the title page, item [30] Foreign Application Priority Data should be:

--[30]  Foreign Application Priority Data

Jun. 13, 1996  [DE]  Germany  .........  19623585--

Signed and Sealed this

Twenty-sixth Day of January, 1999

Attest:

Attesting Officer

*Acting Commissioner of Patents and Trademarks*